United States Patent [19]

Alexson

[11] Patent Number: 4,872,452
[45] Date of Patent: Oct. 10, 1989

[54] BONE RASP

[75] Inventor: Charles E. Alexson, Amery, Wis.

[73] Assignee: Minnesota Mining and Manufacturing Company, St. Paul, Minn.

[21] Appl. No.: 295,254

[22] Filed: Jan. 9, 1989

[51] Int. Cl.⁴ .............................................. A61F 5/04
[52] U.S. Cl. ................. 128/92 VJ; 128/305; 29/78; 30/276; 30/279.2
[58] Field of Search ............... 128/92, 305, 305 R, 128/928, 92 R, 92 EB, 312, 303 R; 29/78, 79, 80, 103 R; 15/236.01, 236.06, 236.08, 93 R, 93 A, 93 B, 93 C; 30/276, 279 R

[56] References Cited

U.S. PATENT DOCUMENTS

| | | | |
|---|---|---|---|
| 10,088 | 10/1853 | Powers | 29/78 |
| D. 272,648 | 2/1984 | Bolesky et al. | D24/28 |
| D. 273,806 | 5/1984 | Bolesky et al. | D24/28 |
| 499,619 | 6/1893 | Weed | 29/78 |
| 2,658,258 | 11/1953 | Hawkinson | 29/78 |
| 2,785,673 | 3/1957 | Anderson | 128/92 |
| 2,820,281 | 1/1958 | Amsen | 29/78 |
| 2,975,504 | 3/1961 | Bentham | 29/78 |
| 2,984,892 | 5/1961 | Oxford et al. | 29/78 |
| 3,298,411 | 1/1967 | Rosett | 146/68 |
| 3,389,447 | 6/1968 | Theobald et al. | 29/78 |
| 3,468,079 | 9/1969 | Kaufman | 51/378 |
| 3,509,611 | 5/1970 | Kifer | 29/78 |
| 3,680,185 | 9/1972 | Wood | 29/79 |
| 3,815,599 | 6/1974 | Deyerle | 128/305 |
| 3,943,934 | 3/1976 | Bent | 128/317 |
| 4,023,572 | 5/1977 | Weigand et al. | 128/305 |
| 4,116,200 | 9/1978 | Braun et al. | 128/305 |
| 4,124,026 | 11/1978 | Berner et al. | 128/303 |
| 4,137,617 | 2/1979 | Newmayer | 29/78 |
| 4,306,550 | 12/1981 | Forte | 128/92 |
| 4,386,609 | 6/1983 | Mongeon | 128/317 |
| 4,552,136 | 11/1985 | Kenna | 128/92 |
| 4,587,964 | 5/1986 | Walker et al. | 128/92 |
| 4,601,289 | 7/1986 | Chiarizzio et al. | 128/305 |
| 4,685,181 | 9/1987 | Schwartz | 29/78 |

Primary Examiner—Robert A. Hafer
Assistant Examiner—Lynda M. Cofsky
Attorney, Agent, or Firm—Donald M. Sell; Walter N. Kirn; Stephen W. Bauer

[57] ABSTRACT

A rasp adapted for rasping generally hard tissue, such as bone, cartilage and associated tissue, and a method of forming such a rasp are disclosed. The rasp comprises a plate-like body having opposite generally parallel major surface portions, and may be detachably attached to a powered device for driving the rasp. A plurality of rasp portions are arranged along the rasp for substantially evenly rasping hard tissue. Each rasp portion has a center, and a plurality of slots through the body extending generally radially outwardly from the center of the portion to define a plurality of cantilever cutting members extending generally radially inwardly of the rasp portion generally toward the center of the rasp portion and separated from one another by the slots. The cutting members are bent to project outwardly from the major surface portions of the body with alternating members of each rasp portion being bent to project outwardly from alternating major surface portions of the body.

17 Claims, 1 Drawing Sheet

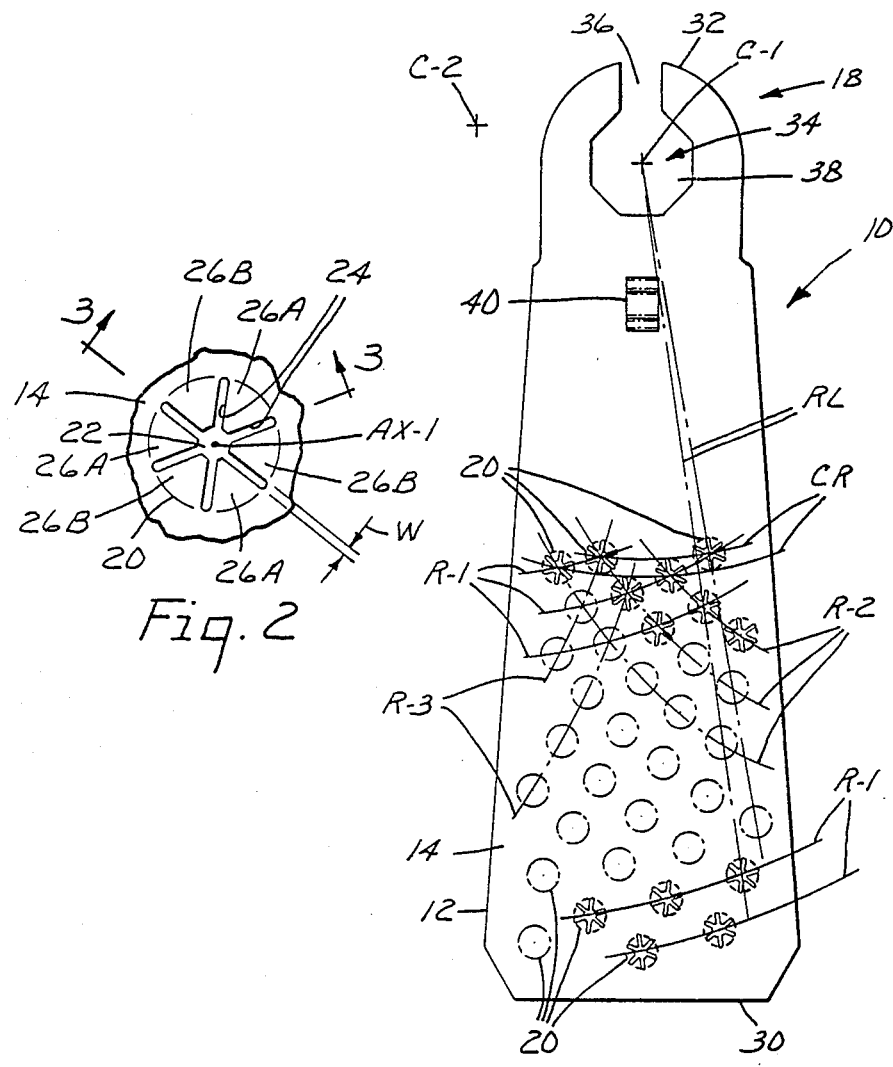
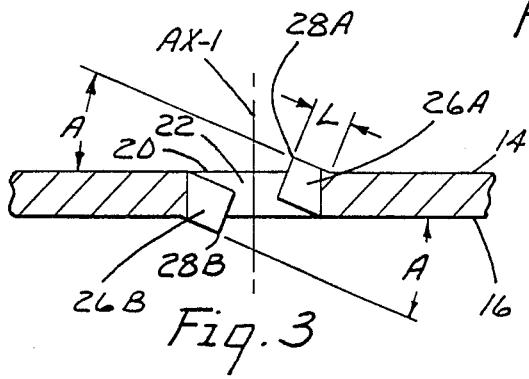

BONE RASP

The invention relates generally to rasps, and more particularly to a rasp adapted for rasping generally hard tissue, such as bone, cartilage and associated tissue.

BACKGROUND OF THE INVENTION

Orthopedic surgeons frequently desire smoother cut surfaces than they have been able to consistently obtain by sawing a section of bone, e.g., for secure engagement with a suitable prosthesis. Sometimes surgeons attempt to smooth out a freshly cut surface by running the side of the saw blade along the surface, possibly leading to bone necrosis (i.e., bone cell death) due to overheating if the saw is run too long. However, if the surgeon does not obtain a sufficiently smooth surface the time required for the patient's recovery may be increased, the strength of a bond between the bone and a prosthesis may be impaired, and the reliability of the prosthesis may even be jeopardized. If the surface is so uneven that substantial portions of the bone remain unloaded, the unloaded portion of the bone may resorb or dissolve into the body, causing further weakening of the bone and the bond between the bone and prosthesis.

SUMMARY OF THE INVENTION

The invention provides a rasp adapted for substantially evenly rasping generally hard tissue, such as bone, cartilage and associated tissue to obtain a smooth surface to, for example, enhance bonding with a prosthesis, and a method of manufacturing such a rasp. The rasp is designed to be readily attached to and detached from a powered surgical device, and is designed to avoid clogging of the cutting surfaces of the rasp by the tissue.

Generally, the rasp of the invention comprises a generally plate-like body having opposite generally parallel major surface portions, and means on the body for detachably attaching the rasp to a powered device for driving the rasp. A plurality of rasp portions are arranged along the rasp for substantially evenly rasping hard tissue. Each rasp portion has a center, and a plurality of slots through the body extending generally radially outwardly from the center of the portion to define a plurality of cantilever cutting members extending generally radially inwardly of the rasp portion generally toward the center of the rasp portion and separated from one another by the slots. The cutting members are bent to project outwardly from the major surface portions of the body, with alternating members of each rasp portion being bent to project outwardly from alternating major surface portions of the body.

The method of manufacturing the rasp includes the steps of providing a hardened stainless steel plate having opposite generally parallel major surfaces, and forming means on the plate for detachably attaching the rasp to a powered device for driving the rasp. A plurality of rasp portions are arranged along the rasp for substantially evenly rasping hard tissue. Each rasp portion is formed by laser cutting a plurality of slots through the body to extend generally radially outwardly from a center to a perimeter to define a plurality of cantilever cutting members extending radially inwardly of the rasp portion, and bending the cutting members to project outwardly from the major surfaces of the body with alternating members of the rasp portion being bent outwardly from alternating respective major surfaces of the body.

Other features will be in part apparent and in part pointed out hereinafter.

BRIEF DESCRIPTION OF THE DRAWING

The invention will be further described with reference to the drawing wherein corresponding reference characters indicate corresponding parts throughout the several views of the drawing, and wherein:

FIG. 1 is a top plan view of a rasp of the invention, illustrating a preferred arrangement of rasp portions along the rasp;

FIG. 2 is an enlarged fragmentary top plan view of one of the rasp portions of FIG. 1; and FIG. 3 is a cross-sectional view substantially along line 3—3 of FIG. 2.

DETAILED DESCRIPTION

As shown in FIG. 1, a rasp of the invention is designated in its entirety by the reference numeral 10. The rasp 10 is adapted for rasping generally hard tissue, such as bone, cartilage and associated tissue. The rasp 10 is designed to be attached to a source of oscillating-pivoting motion via some type of releasable attaching mechanism (not shown), such as the attaching assembly for an osteotomy saw blade disclosed in coassigned U.S. Pat. No. 4,386,609, which is incorporated herein by reference, or the quick release mechanism for surgical devices disclosed in coassigned U.S. Pat. No. 3,943,934, which is also incorporated herein by reference. As used herein, "rasp" refers to a rasp blade, body or generally plate-like structure, and is not intended to be limited to such a rasp blade, body or plate-like structure in combination with a power source, or the mechanism for attaching the rasp to the power source.

The rasp 10 generally comprises an elongate generally plate-like body 12 of hardened stainless steel, such as 301/302 SST full hard stainless steel. The body 12 has opposite generally parallel major surface portions or sides 14 and 16, and a thickness between the surfaces 14 and 16 of, for example, approximately 1 mm (0.04 in.). Means 18 is provided on the body 12 for detachably attaching the rasp 10 to a powered device (not shown) for driving the rasp 10, for example, via one of the attaching assemblies discussed above. A plurality of rasp portions 20 are suitably arranged along the rasp 10 for substantially evenly rasping hard tissue.

As shown in FIG. 2, each rasp portion 20 has an open center 22, and a plurality of slots 24 through the body 12 extending generally radially outwardly from the center 22 of the portion 20. The slots 24 define a plurality (e.g., 6) of cantilever cutting members 26A, 26B extending generally radially inwardly of the rasp portion 20 generally toward the center 22 of the rasp portion 20. The cutting members 26A, 26B are separated from one another by the slots 24. The cutting members 26A, 26B are bent to project outwardly from the major surface portions 14 and 16 of the body 12, with alternating members 26A or 26B of each rasp portion 20 being bent to project outwardly from alternating respective major surface portions 14 or 16 of the body 12 so that either surface portion 14 or 16 may be used for rasping. That is, the three cutting members designated 26A are bent to project outwardly of respective surface portion 14 (upwardly in FIG. 3), and the three cutting members designated 26B are bent to project outwardly of respective surface portion 16 (downwardly in FIG. 3).

The center 22 and slots 24 of each rasp portion 20 are preferably laser-cut through the body by a carbon-dioxide laser, such as the laser sold under the trade designation "Trumatic 180 type 93031" by Trumpf G.m.b.H. & C. of Ditzingen, West Germany or the "Model VA15" laser sold by Lumonics Material Processing Corp. of Eden Prairie, Minnesota. Each slot 24 is cut to have a width W (FIG. 2) sufficiently great to permit rasped tissue to flow through the slots 24 during rasping (e.g., a width W of approximately 0.1–1 mm, preferably 0.2 mm, separating adjacent cutting members).

Each cutting member 26A, 26B is generally triangular (FIG. 2), and has a free cutting point 28A or 28B spaced approximately 0.2–2 mm (preferably 0.3–0.7 mm) from the respective major surface portion 14 or 16 of the bosy 12. The perimeter of each rasp portion 20 is generally hexagonal, as defined by the attached bases of the six cutting members 26A, 26B. Each cutting member 26A, 26B extends generally radially inwardly from a respective side of the hexagonal perimeter toward the center 22 of the rasp portion 20. The cutting members 26A, 26B are bent outwardly from the major surface portions 14 and 16 of the body 12 at an angle A (FIG. 3) of approximately 10–45 degrees (preferably 20–25 degrees) with respect to the respective major surface portion 14 or 16, and each cutting member 26A, 26B has a length L of approximately 2–4 mm (e.g., 2.4 mm) between the free cutting point 28A or 28B and the perimeter of the rasp portion 20. The free cutting points 28A, 28B of the members 26A and 26B of each rasp portion 20 approximately define surface points along an imaginary cylinder having a diameter of approximately 0.1–3 mm (e.g., 0.8 mm), and a central longitudinal axis AX-1 generally perpendicular to the major surface portions 14 and 16 of the body 12.

As shown in FIG. 1, the rasp portions 20 are arranged in a pattern wherein there is increasing spacing between the rasp portions 20 in the direction away from the center C-1 of the attaching means 18 (downwardly in FIG. 1), which is also the center of pivoting-oscillating motion when the rasp 10 is being used. For example, the rasp portions 20 may be arranged along substantially equally-spaced radial lines RL extending generally radially outwardly from the center C-1 of the attaching means 18 at approximately two degree intervals. Because the radial lines RL diverge from one another in the direction away from the center C-1 of the attaching means 18, the rasp portions 20 are spaced farther apart adjacent the outward end 30 (downward end in FIG. 1) of the rasp 10 than they are closer to the center C-1. Greater spacing of cutting surfaces (rasp portions) adjacent the outward end 30 facilitates even rasping of tissue, since the outward end 30 of the rasp 10 is the fastest moving part of the rasp during use.

More specifically, the rasp portions 20 are arranged along the radial lines RL in staggered arcuate rows R-1 (and preferably R-2 and R-3) extending obliquely with respect to the radial lines RL and with respect to the direction of oscillating motion. The rasp portions 20 of any row R-1, R-2, or R-3 are staggered with respect to the intended direction of motion of the rasp 10. For example, each row R-1 is staggered with respect to one of the series of circumferences CR about the center C-1 of the attaching means 18 that are arranged serially outwardly from the center C-1. The intersecting arcuate rows R-1, R-2, and R-3, along which the rasp portions 20 are arranged, are preferably substantially centered with respect to an axis or center offset from the center C-1 of the attaching means 18 (e.g., R-1 may be arcuate about a center C-2). Rows R-1 are preferably spaced farther apart in the direction toward the outward end 30 of the rasp 10.

The attaching means 18 may comprise a specially-configured inward end portion 32 (FIG. 1) of the body 12 opposite the outward end 30, similar to the end portion described in coassigned U.S. Pat. No. 4,386,609 (incorporated herein by reference), although other types of attaching means are also contemplated. A through aperture 34 is formed between the major surface portions 14 and 16. The through aperture 34 includes a narrow aperture portion 36 defined by spaced parallel walls opening through the inward (upward in FIG. 1) end or edge of the body 12, and a larger aperture portion 38 spaced from the inward edge of the body 12 and defined by octagonally arranged walls, as illustrated in FIG. 1, but which could be defined by a circular wall. A projection 40 from one of the major surface portions, e.g., 14, may be provided generally adjacent the through aperture 34 centrally of the width of the body 12 and between the aperture 34 and the rasp portions 20.

As various changes could be made in the above constructions and methods without departing from the scope of the invention, it is intended that all matter contained in the above description or shown in the accompanying drawing be interpreted as illustrative and not in a limiting sense.

I claim:

1. A rasp adapted for rasping generally hard tissue, such as bone, cartilage and associated tissue, the rasp comprising a generally plate-like body having opposite generally parallel major surface portions, an attaching means having a center for detachably attaching the rasp to a powered device for driving the rasp, and a plurality of rasp portions arranged along the rasp for substantially evenly rasping hard tissue, each rasp portion having a center, and a plurality of slots through the body extending generally radially outwardly from the center of the portion to define a plurality of cantilever cutting members extending generally radially inwardly of the rasp portion generally toward the center of the rasp portion and separated from one another by the slots, the cutting members being bent to project outwardly from the major surface portions of the body with alternating members of each rasp portion being bent to project outwardly from opposite surface portions of the body.

2. A rasp according to claim 1 wherein the slots have a width sufficiently great to permit rasped tissue to flow through the slots during rasping.

3. A rasp according to claim 2 wherein the slots have a width of approximately 0.1–1 mm separating adjacent cutting members.

4. A rasp according to claim 3 wherein the center and slots of each rasp portion are laser-cut through the body.

5. A rasp according to claim 3 wherein each cutting member is generally triangular, and has a free cutting point spaced approximately 0.2–2 mm from a respective major surface portion of the body.

6. A rasp according to claim 5 wherein each rasp portion has a generally hexagonal perimeter, and comprises six of the aforesaid cutting members, each cutting member extending generally radially inwardly from a respective side of the hexagonal perimeter toward the center of the rasp portion, the cutting members being bent outwardly from a respective major surface portion of the body at an angle of approximately 10–45 degrees with respect to the major surface portions of the body, each cutting member having a length of approximately 2–4 mm between the free cutting point and the perimeter of the rasp portion, the free cutting points of the members of each rasp portion approximately defining surface points along a cylinder having a diameter of approximately 0.1–3 mm and a central longitudinal axis generally perpendicular to the major surface portions of the body.

7. A rasp according to claim 1 wherein the attaching means is adapted for detachably attaching the rasp to a source of oscillating motion, the rasp portions being arranged along substantially equally-spaced radial lines extending generally radially outwardly from the center of the attaching means so that the rasp portions are arranged along substantially equally-spaced lines extending generally radially outwardly from the center of oscillating motion when the rasp is oscillating.

8. A rasp according to claim 7 wherein the rasp portions are arranged along the radial lines in staggered rows extending obliquely with respect to the radial lines and with respect to the direction of oscillating motion.

9. A rasp according to claim 8 wherein the rasp portions are also arranged along arcs centered with respect to an axis offset from the attaching means.

10. A rasp according to claim 1 wherein the body is of hardened stainless steel having a thickness of approximately 1mm, the center and slots of each rasp portion being laser-cut through the body by a carbon-dioxide laser.

11. A method of manufacturing a rasp adapted for rasping generally hard tissue, such as bone, cartilage and associated tissue, the method comprising the following steps:
providing a hardened stainless steel plate having opposite generally parallel major surfaces;
forming an attaching means having a center on the plate for detachably attaching the rasp to a powered device for driving the rasp; and
forming a plurality of rasp portions arranged along the rasp for substantially evenly rasping hard tissue, including the steps of forming each rasp portion by:
laser cutting a plurality of slots through the body to extend generally radially outwardly from a center to a perimeter to define a plurality of cantilever cutting members extending radially inwardly of the rasp portion; and
bending the cutting members to project outwardly from the major surfaces of the body with alternating members of the rasp portion being bent outwardly from alternating respective major surfaces of the body.

12. A method according to claim 11 wherein the step of laser-cutting a plurality of slots includes laser-cutting the slots to have a width of approximately 0.1–1 mm separating adjacent cutting members.

13. A method according to claim 12 wherein the step of laser-cutting a plurality of slots includes cutting the slots to define the cutting members as generally triangular, and having a free cutting point, and the step of bending the cutting members includes bending each cutting member such that its free cutting point is spaced approximately 0.2–2 mm from its respective major surface of the body.

14. A method according to claim 13 wherein the step of laser-cutting a plurality of slots includes cutting the slots with a carbon dioxide laser to define six of the aforesaid cutting members in each rasp portion, with each cutting member having a length of approximately 2–4 mm extending generally radially inwardly from a respective side of a hexagonal perimeter of the portion to the free cutting point; the step of bending the cutting members including bending the members outwardly from the opposite major surfaces of the body at an angle of approximately 10–45 degrees with respect to the major surfaces of the body, with the free cutting points of the members of each rasp portion approximately defining surface points along a cylinder having a diameter of approximately 0.1–3 mm and a central longitudinal axis generally perpendicular to the major surfaces of the body.

15. A method according to claim 11 wherein the attaching means is adapted for detachably attaching the rasp to a source of oscillating motion, the step of forming rasp portions including the step of arranging the rasp portions along substantially equally-spaced radial lines extending generally radially outwardly from the center of the attaching means so that the rasp portions are arranged along substantially equally-spaced lines extending generally radially outwardly from the center of oscillating motion when the rasp is oscillating.

16. A method according to claim 15 wherein the step of arranging the rasp portions further includes arranging the rasp portions along the radial lines in staggered rows extending obliquely with respect to the radial lines and with respect to the direction of oscillating motion.

17. A rasp according to claim 16 wherein the step of arranging the rasp portions further includes arranging the rasp portions along arcs centered with respect to an axis offset from the attaching means.

* * * * *